United States Patent
DeMoss et al.

(10) Patent No.: US 10,544,339 B2
(45) Date of Patent: Jan. 28, 2020

(54) COLD-TOLERANT SEALANTS AND COMPONENTS THEREOF

(71) Applicant: 3M INNOVATIVE PROPERTIES COMPANY, St. Paul, MN (US)

(72) Inventors: Susan E. DeMoss, Stillwater, MN (US); Jonathan D. Zook, Stillwater, MN (US); Matthew Capel, Huntington Beach, CA (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/400,092

(22) Filed: May 1, 2019

(65) Prior Publication Data

US 2019/0256752 A1    Aug. 22, 2019

Related U.S. Application Data

(62) Division of application No. 15/545,849, filed as application No. PCT/US2016/017347 on Feb. 10, 2016, now Pat. No. 10,287,466.

(60) Provisional application No. 62/116,019, filed on Feb. 13, 2015.

(51) Int. Cl.
| | |
|---|---|
| *C09J 181/02* | (2006.01) |
| *C08G 75/02* | (2016.01) |
| *C08L 81/00* | (2006.01) |
| *C08G 75/12* | (2016.01) |
| *C08G 75/04* | (2016.01) |
| *C08L 81/02* | (2006.01) |
| *C08G 75/00* | (2006.01) |
| *C07C 323/14* | (2006.01) |
| *C07C 321/18* | (2006.01) |

(52) U.S. Cl.
CPC ........... *C09J 181/02* (2013.01); *C07C 321/18* (2013.01); *C07C 323/14* (2013.01); *C08G 75/00* (2013.01); *C08G 75/02* (2013.01); *C08G 75/04* (2013.01); *C08G 75/12* (2013.01); *C08L 81/00* (2013.01); *C08L 81/02* (2013.01)

(58) Field of Classification Search
CPC ........ C09J 181/02; C08G 75/12; C08G 75/04; C07C 321/18; C07C 323/14
See application file for complete search history.

(56) References Cited

U.S. PATENT DOCUMENTS

| | | | |
|---|---|---|---|
| 2,664,414 A | 12/1963 | Morris | |
| 3,673,260 A | 6/1972 | Esclamadon | |
| 4,136,086 A | 1/1979 | Baumann | |
| 4,366,307 A | 12/1982 | Singh | |
| 4,609,762 A | 9/1986 | Morris | |
| 5,225,472 A | 7/1993 | Cameron | |
| 5,324,858 A | 6/1994 | Aberkane | |
| 5,415,794 A | 5/1995 | Aberkane | |
| 5,430,112 A | 7/1995 | Sakata | |
| 5,464,910 A | 11/1995 | Nakatsuka | |
| 5,593,795 A | 1/1997 | Chen | |
| 5,912,319 A | 6/1999 | Zook | |
| 5,959,071 A | 9/1999 | DeMoss | |
| 6,172,179 B1 | 1/2001 | Zook | |
| 6,232,401 B1 | 5/2001 | Zook | |
| 6,372,849 B2 | 4/2002 | DeMoss | |
| 6,486,297 B2 | 11/2002 | Zook | |
| 6,509,418 B1 | 1/2003 | Zook | |
| 6,605,687 B1 | 8/2003 | Gross | |
| 6,605,689 B1 | 8/2003 | Gross | |
| 6,605,690 B1 | 8/2003 | Gross | |
| 6,605,691 B1 | 8/2003 | Gross | |
| 6,605,692 B1 | 8/2003 | Gross | |
| 7,097,883 B2 | 8/2006 | Sawant | |
| 7,390,859 B2 | 6/2008 | Sawant | |
| 7,622,548 B2 | 11/2009 | Rao | |
| 7,671,145 B2 | 3/2010 | Sawant | |
| 7,687,578 B2 | 3/2010 | Zook | |
| 7,834,105 B2 | 11/2010 | Sawant | |

(Continued)

FOREIGN PATENT DOCUMENTS

| | | | | |
|---|---|---|---|---|
| JP | 04077576 | * | 3/1992 | ............ C08G 75/02 |
| JP | 2005251556 | | 9/2005 | |
| WO | WO 2007-050725 | | 5/2007 | |
| WO | WO 2008-137198 | | 11/2008 | |
| WO | WO 2009-131796 | | 10/2009 | |
| WO | WO 2012-093510 | | 7/2012 | |

OTHER PUBLICATIONS

"Flexible, One-Part Epoxy Adhesive Composition" IP.com Prior Art Database Technical Disclosure, Feb. 11, 2016, 2 pages.

(Continued)

*Primary Examiner* — Shane Fang
(74) *Attorney, Agent, or Firm* — 3M IPC; Carlos M. Téllez

(57) ABSTRACT

Polythioether polymers, sealants containing polythioether polymers, and compounds useful as stabilizing monomers in the manufacture of polythioether polymers are provided. In many embodiments the polymers and sealants demonstrate reduced risk of spoilage that may be caused by low temperature storage of the polymer or uncured sealant. Compounds useful as stabilizing monomers include compounds according to formula I:

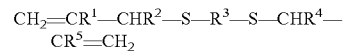

wherein $R^1$, $R^2$, $R^4$ and $R^5$ are independently selected from —H, —$CH_3$ or —$C_2H_5$, and
wherein $R^3$ is selected from divalent groups comprising 2-12 carbon atoms, 0-5 ether oxygen atoms and 0-5 thioether sulfur atoms, which may be straight, branched or cyclic.

24 Claims, No Drawings

(56) References Cited

U.S. PATENT DOCUMENTS

| | | |
|---|---|---|
| 7,858,703 B2 | 12/2010 | Zook |
| 7,858,704 B2 | 12/2010 | Sawant |
| 7,875,666 B2 | 1/2011 | Gilmore |
| 7,879,955 B2 | 2/2011 | Rao |
| 7,888,436 B2 | 2/2011 | Szymanski |
| 8,076,420 B2 | 12/2011 | Sawant |
| 8,084,519 B2 | 12/2011 | Okuno |
| 8,138,273 B2 | 3/2012 | Rao |
| 2002/0007015 A1 | 1/2002 | DeMoss |
| 2003/0008977 A1 | 1/2003 | Zook |
| 2004/0039121 A1 | 2/2004 | Zook |
| 2004/0247792 A1 | 12/2004 | Sawant |
| 2005/0010003 A1 | 1/2005 | Sawant |
| 2006/0175005 A1 | 8/2006 | Sawant |
| 2006/0270796 A1 | 11/2006 | Sawant |
| 2007/0287810 A1 | 12/2007 | Rao |
| 2009/0069407 A1 | 3/2009 | Gries |
| 2010/0010133 A1 | 1/2010 | Zook |
| 2011/0060091 A1 | 3/2011 | Sawant |
| 2013/0165600 A1 | 6/2013 | Chen |

OTHER PUBLICATIONS

3M™ One Part Epoxy Adhesive, Product Introduction, 3 pages.

Ameduri, "Synthesis of telechelic monodispersed dithiols", Polymer Bulletin, Apr. 1991, No. 26, pp. 377-382.

Cai, "Synthesis of Poly(thioether ether)s from Diallyl Ether", American Chemical Society, Polymer Preprints, Apr. 1995, vol. 36, No. 1, pp. 243-244.

Kharasch, Organic Sulfur Compounds, 260-263 (1961).

Marvel, "Polyalkylene Sulfides. VI. New Polymers Capable of Cross-Linking", Journal of Polymer Science, 1951, vol. 6, No. 6, pp. 711-716.

Marvel, "Polyalkylene Sulfides. X. The Reaction of Hexamethylenedithiol with 1,3-Butadiene", Journal of Polymer Science, 1952, vol. 8, No. 3, pp. 313-320.

Moorhoff, "Novel synthesis of symmetrical 3,3'-allyl dithioethers as photoplastic monomer precursors by equal molar rate addition of reactants and solvent controlled oligomenzation", Monatsh Chem. 2013, vol. 144, pp. 891-902.

Moorhoff, "Synthesis of novel ([oligomethylene] alkane-α,ω-diyl) bis(diallylcarbamodithioates); monomers as precursors for RAFT photoplastic polymer networks", Canadian Journal of Chemistry, 2014, vol. 92, No. 1, pp. 19-25.

Nuyken, "Telechelics via addition of dithiols onto alkadienes, $2^{a)}$ Base and acid catalysis", Macromolecular Chemistry and Physics, 1990, vol. 191, No. 10, pp. 2465-2473.

OAE, Organic Chemistry of Sulfur, 129-130 (1977).

OAE, Organic Chemistry of Sulfur, 408-418, (1977).

Saville, "Acid-catalyzed Addition of Thiols to Conjugated Dienes", Journal of the Chemical Society, Jan. 1962, pp. 5040-5045.

Yamaguchi, "Reaction of thiol to diene polymer in the presence of various catalysts", Polymer, Mar. 1973, vol. 14, pp. 87-90.

Roberts et al., "A Convenient Synthesis of Polysulfides by Phase Transfer Catalysis," Phosphorus, Sulfur, and Silicon, vol. 83, pp. 49-51, 1993.

Hutchison et al., "A novel tin (II) dithioether complex," Journal of Organometallic Chemistry, vol. 691, pp. 1658-1660, 2006.

International Search Report for PCT International Application No. PCT/US2016/017347, dated May 13, 2016, 5 pages.

\* cited by examiner

US 10,544,339 B2

COLD-TOLERANT SEALANTS AND COMPONENTS THEREOF

FIELD OF THE DISCLOSURE

This disclosure relates to polythioether polymers, sealants containing polythioether polymers, and stabilizing monomers useful in the manufacture of polythioether polymers. In many embodiments the polymers and sealants demonstrate reduced risk of spoilage that may be caused by low temperature storage of the polymer or uncured sealant.

BACKGROUND OF THE DISCLOSURE

Certain embodiments of polythioether polymer-based sealants are known in the art. The following references may be relevant to such a technology: U.S. Pat. Nos. 5,912,319; 5,959,071; 6,172,179; 6,232,401; 6,372,849; 6,486,297; 6,509,418; 7,097,883; 7,390,859; 7,622,548; 7,671,145; 7,687,578; 7,834,105; 7,858,703; 7,858,704; 7,875,666; 7,879,955; 7,888,436; 8,076,420; and 8,138,273.

SUMMARY OF THE DISCLOSURE

Briefly, the present disclosure provides a compound according to formula I:

$$CH_2=CR^1-CHR^2-S-R^3-S-CHR^4-CR^5=CH_2 \quad [I]$$

where $R^1$, $R^2$, $R^4$ and $R^5$ are independently selected from —H, —$CH_3$ or —$C_2H_5$, and where $R^3$ is selected from divalent groups comprising 2-12 carbon atoms, 0-5 ether oxygen atoms and 0-5 thioether sulfur atoms, which may be straight, branched or cyclic. In some embodiments, $R^1$ and $R^5$ are the same and are selected from —H and —$CH_3$. In some embodiments, $R^2$ and $R^4$ are the same and are selected from —H and —$CH_3$. In some embodiments, $R^1$ and $R^5$ are —$CH_3$ and $R^2$ and $R^4$ are —H. In some embodiments, $R^3$ is a divalent group according to formula II:

$$-((CH_2)_n-X)_m-(CH_2)_n- \quad [II]$$

where m is 0-5, each n is independently selected from 2-6, and each X is independently selected from O or S. Additional embodiments of the compounds of the present disclosure are described below under "Selected Embodiments." The compounds of the present disclosure may be useful as stabilizing diene monomers in the synthesis of polythioether polymers, such as for use in sealants.

In another aspect, the present disclosure provides a polythioether polymer which is a copolymer of one or more compounds according to the present disclosure (stabilizing diene monomers). In some embodiments, the polythioether polymer is a copolymer of one or more compounds according to the present disclosure with one or more polythiols and one or more polyepoxides. In some embodiments, the polythiol is a dithiol according to formula VI:

$$HS-R^6-SH \quad [VI]$$

where $R^6$ is selected from divalent groups comprising 2-12 carbon atoms, 0-5 ether oxygen atoms and 0-5 thioether sulfur atoms, which may be straight, branched or cyclic. In some embodiments, $R^6$ of the dithiol is the same group as $R^3$ of the stabilizing diene monomer. In some embodiments, $R^6$ is a divalent group according to formula II:

$$-((CH_2)_n-X)_m-(CH_2)_n- \quad [II]$$

where m is 0-5, each n is independently selected from 2-6, and each X is independently selected from O or S. In some embodiments, the polythioether polymer is a thiol-terminated polymer. In some embodiments, the polythioether polymer comprises stabilizing units which are segments derived from stabilizing diene monomers, where the stabilizing units comprise greater than 1.1 weight % of the polymer and less than 24 weight % of the polymer. In some embodiments, the polythioether polymer comprises epoxy units which are segments derived from polyepoxides, where the epoxy units comprise greater than 1.1 weight % of the polymer and less than 20 weight % of the polymer. In some embodiments, the polythioether polymer is derived from a reaction mixture comprising a molar excess of polythiols over other reactive species of greater than 101/99. Additional embodiments of the polythioether polymers of the present disclosure are described below under "Selected Embodiments."

In another aspect, the present disclosure provides a polythioether polymer comprising divalent groups in the polymer backbone according to formula XI:

$$-S-R^{11}-S-CH_2-CHR^{12}-CHR^{13}-S- \quad [XI]$$

where $R^{11}$ is selected from divalent groups comprising 2-12 carbon atoms, 0-5 ether oxygen atoms and 0-5 thioether sulfur atoms, which may be straight, branched or cyclic; and where $R^{12}$ and $R^{13}$ are independently selected from —H, —$CH_3$ or —$C_2H_5$, provided that at least one of $R^{12}$ and $R^{13}$ is not —H. In some embodiments, the polythioether polymer comprises divalent groups in the polymer backbone according to formula XII:

$$-C(OH)(R^{14})-CH_2-S-R^{11}-S-CH_2-CHR^{12}-CHR^{13}-S- \quad [XII]$$

where $R^{14}$ is selected from —H or $C_{1-4}$ alkyl. In some embodiments, the polythioether polymer comprises divalent groups in the polymer backbone according to formula XIII:

$$-S-R^{11}-S-CH_2-CHR^{12}-CHR^{13}-S-R^{15}-S- \quad [XIII]$$

where $R^{15}$ is selected from divalent groups comprising 2-12 carbon atoms, 0-5 ether oxygen atoms and 0-5 thioether sulfur atoms, which may be straight, branched or cyclic. In some embodiments, $R^{15}$ is the same group as $R^{11}$. In some embodiments, $R^{12}$ is —$CH_3$ and $R^{13}$ is —H. In some embodiments, $R^{11}$ is a divalent group according to formula II:

$$-((CH_2)_n-X)_m-(CH_2)_n- \quad [II]$$

where m is 0-5, each n is independently selected from 2-6, and each X is independently selected from O or S. In some embodiments, the polythioether polymer is a thiol-terminated polymer. Additional embodiments of the polythioether polymers of the present disclosure are described below under "Selected Embodiments."

In another aspect, the present disclosure provides a polythioether polymer comprising divalent groups in the polymer backbone according to formula XXI:

$$-S-R^{21}-S-CH(CH_3)-CH_2-S- \quad [XXI]$$

where $R^{21}$ is selected from divalent groups comprising 2-12 carbon atoms, 0-5 ether oxygen atoms and 0-5 thioether sulfur atoms, which may be straight, branched or cyclic. In some embodiments this polythioether polymer comprises divalent groups in the polymer backbone according to formula XXIII:

$$-S-R^{21}-S-CH(CH_3)-CH_2-S-R^{23}-S- \quad [XXIII]$$

where $R^{23}$ is the same group as $R^{21}$. Additional embodiments of the polythioether polymers of the present disclosure are described below under "Selected Embodiments."

In another aspect, the present disclosure provides a sealant comprising any of the polythioether polymers of the present disclosure and a curing agent. In some embodiments, the curing agent is a crosslinking agent. In some embodiments, the curing agent comprises a polyepoxide. Additional embodiments of sealants of the present disclosure are described below under "Selected Embodiments."

In another aspect, the present disclosure provides a material obtained by curing a sealant according to the present disclosure. Additional embodiments of cured materials of the present disclosure are described below under "Selected Embodiments."

DETAILED DESCRIPTION

The present disclosure provides polythioether polymer-based sealants. In many embodiments, the sealants according to the present disclosure may be stored in the uncured state at low temperatures with reduced risk of performance loss. In addition, the present disclosure provides certain polythioether polymers and monomers for use in polythioether polymers.

Aerospace Sealants

The present disclosure provides polythioether polymer-based sealants, including sealants useful in the aerospace industry. In some applications, sealants according to the present disclosure may be used to seal fuel tanks. In these applications, sealants preferably exhibit lower density, more rapid cure, higher tensile strength after cure, high flexibility at low temperature after cure, high jet fuel resistance after cure (as measured by standard industry methods), and low Tg after cure, typically below −50° C., more typically below −53° C., and more typically below −55° C. The polythioether polymers comprising these sealants preferably exhibit lower density and low Tg, typically below −50° C., more typically below −53° C., and more typically below −55° C.

In addition, the uncured sealants according to the present invention preferably exhibit resistance to clouding, crystallizing, or seeding when stored at low temperatures. In some embodiments, the sealant exhibits substantially no solids formation in 32 weeks of storage at 4.4° C.; in some embodiments the sealant exhibits substantially no solids formation in 24 weeks of storage at 4.4° C.; in some embodiments the sealant exhibits substantially no solids formation in 16 weeks of storage at 4.4° C.; in some embodiments the sealant exhibits substantially no solids formation in 8 weeks of storage at 4.4° C. In some of the preceding embodiments, "substantially no solids formation" means no visible solids formation; in some embodiments, "substantially no solids formation" means no visible clouding; and in some embodiments, "substantially no solids formation" means not more than 5 volume % conversion to solids. In some embodiments, the polythioether polymer comprising the sealant exhibits substantially no solids formation in 32 weeks of storage at 4.4° C.; in some embodiments the sealant exhibits substantially no solids formation in 24 weeks of storage at 4.4° C.; in some embodiments the sealant exhibits substantially no solids formation in 16 weeks of storage at 4.4° C.; in some embodiments the sealant exhibits substantially no solids formation in 8 weeks of storage at 4.4° C. In some of the preceding embodiments, "substantially no solids formation" means no visible solids formation; in some embodiments, "substantially no solids formation" means no visible clouding; and in some embodiments, "substantially no solids formation" means not more than 5 volume % conversion to solids.

Stabilizing Diene Monomers

The present disclosure provides compounds according to formula I:

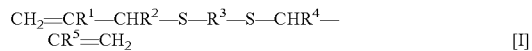

where $R^1$, $R^2$, $R^4$ and $R^5$ are independently selected from —H, —CH$_3$ or —C$_2$H$_5$, and $R^3$ is selected from divalent groups comprising 2-12 carbon atoms, 0-5 ether oxygen atoms and 0-5 thioether sulfur atoms, which may be straight, branched or cyclic. Typically $R^1$, $R^2$, $R^4$ and $R^5$ are independently selected from —H and —CH$_3$. In some embodiments, one of $R^1$ and $R^2$ is —H and the other is —CH$_3$ and one of $R^4$ and $R^5$ is —H and the other is —CH$_3$. Typically $R^1$ and $R^5$ are the same and $R^2$ and $R^4$ are the same. In some embodiments, $R^1$ and $R^5$ are —CH$_3$ and $R^2$ and $R^4$ are —H. In some embodiments, $R^1$ and $R^5$ are —H and $R^2$ and $R^4$ are —CH$_3$. In some embodiments, $R^1$, $R^2$, $R^4$ and $R^5$ are —H.

In some embodiments, $R^3$ is a divalent group according to formula II:

where m is 0-5, each n is independently selected from 2-6, and each X is independently selected from O or S. In some embodiments, $R^3$ is a divalent group according to formula III:

where m is 0-5, and each X is independently selected from O or S.

The compounds may be synthesized by any suitable method. In some embodiments, HS—$R^3$—SH is reacted with species such as CH$_2$=CR$^1$—CHR$^2$—Y or Y—CHR$^4$—CR$^5$=CH$_2$ where Y is a halogen, typically selected from Cl or Br.

These compounds are useful as diene monomers in the synthesis of polythioether polymers, and in particular as stabilizing diene monomers in the synthesis of polythioether polymers for use in sealants.

Polythioether Polymers

The present disclosure provides polythioether polymers that are copolymers the stabilizing diene monomers according to the present disclosure, typically with one or more polythiols. In some embodiments, the polythioether polymer is furthermore a copolymer of additional dienes, other than the stabilizing diene monomers according to the present disclosure. In some embodiments, the polythioether polymer is furthermore a copolymer of additional monomers or oligomers which are reactive with polythiols; in some such embodiments the additional monomers or oligomers are polyepoxides. In some embodiments, the polythioether polymer is furthermore a copolymer of additional monomers or oligomers which are reactive with dienes. In some embodiments, the polythioether polymer is a vinyl-terminated polymer. In some embodiments, the polythioether polymer is a thiol-terminated polymer.

In some embodiments, the polythiol is a dithiol according to formula VI:

wherein $R^6$ is selected from divalent groups comprising 2-12 carbon atoms, 0-5 ether oxygen atoms and 0-5 thioether sulfur atoms, which may be straight, branched or cyclic. In some embodiments, the dithiol is the same as a dithiol used in the synthesis of the stabilizing diene monomer.

In some embodiments, a polyepoxide is additionally incorporated into the polythioether polymer. Any suitable polyepoxides may be used. In some embodiments, the polyepoxide is a diepoxide. In some embodiments the polyepoxide has a functionality greater than 2. Suitable polyepoxides may include those according to formula XXX:

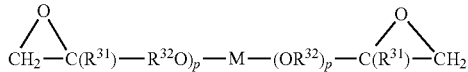
[XXX]

wherein group M is C2-10 alkyl, C6-20 aryl, C6-20 aryl substituted with at least one C1-8 alkyl group, or a N or O heteroatom. Suitable polyepoxide compounds operative herein are recited in U.S. Pat. No. 4,136,086. In some embodiments, polyepoxides according to the present invention contain an aryl group within M. It has been discovered that an aryl backbone component synergistically operates with the hydroxyl groups associated with thiol epoxide reaction to form a polythioether polymer with superior strength and handling. $R^{31}$ is hydrogen or C1-C4 alkyl group, more typically hydrogen or a methyl group. $R^{32}$ is selected from divalent groups comprising 1-12 carbon atoms, 0-5 ether oxygen atoms and 0-5 thioether sulfur atoms, which may be straight, branched or cyclic. P is an integer value ranging from 1 to 10. In some embodiments, suitable polyepoxides may include the diglycidylether of bisphenol A (such as EPON 828®, Shell Chemicals Ltd.), diglycidylether of 55 bisphenol F (such as ERISYST™, CVC), any of the lower functionality Novolaks (such as DEN 43FM, The Dow Chemical Co.), as well as butane- and hexane-diol diglycidyl ether (such as ARALDITE®, Ciba-Geigy).

In some embodiments, Markovnikov addition of thiol groups of the dithiol to unsaturated groups of the stabilizing diene monomer results in a polythioether polymer which includes divalent groups in the polymer backbone according to formula XI:

—S—$R^{11}$—S—$CH_2$—$CHR^{12}$—$CHR^{13}$—S— [XI]

where $R^{11}$ is selected from divalent groups comprising 2-12 carbon atoms, 0-5 ether oxygen atoms and 0-5 thioether sulfur atoms, which may be straight, branched or cyclic; and $R^{12}$ and $R^{13}$ are independently selected from —H, —$CH_3$ or —$C_2H_5$, provided that at least one of $R^{12}$ and $R^{13}$ is not —H.

In addition, anti-Markovnikov addition of thiol groups of the dithiol to unsaturated groups of the stabilizing diene monomer may provide divalent groups in the polymer backbone according to formula XIV:

—S—$R^{11}$—S—$C(CH_3)R^{12}$—$CHR^{13}$—S— [XIV]

wherein $R^{11}$, $R^{12}$ and $R^{13}$ are as defined above.

In some embodiments, which are copolymers of a dithiol, a stabilizing diene monomer, and a polyepoxide, the polythioether polymer will include divalent groups in the polymer backbone according to formula XII:

—C(OH)($R^{14}$)—$CH_2$—S—$R^{11}$—S—$CH_2$—$CHR^{12}$—$CHR^{13}$—S— [XII]

where $R^{14}$ is selected from —H or $C_{1-4}$ alkyl; and $R^{11}$, $R^{12}$ and $R^{13}$ are as defined above.

In some embodiments, where the stabilizing diene monomer is according to formula XL:

$CH_2$=CH—$CH_2$—S—$R^3$—S—$CH_2$—CH=$CH_2$ [XL]

where $R^3$ is as described herein, anti-Markovnikov addition of thiol groups of the dithiol to unsaturated groups of the stabilizing diene monomer will provide divalent groups in the polymer backbone according to formula XXI:

—S—$R^{21}$—S—$CH(CH_3)$—$CH_2$—S— [XXI]

where $R^{21}$ is selected from divalent groups comprising 2-12 carbon atoms, 0-5 ether oxygen atoms and 0-5 thioether sulfur atoms, which may be straight, branched or cyclic. Since anti-Markovnikov addition is disfavored, the amount of stabilizing diene monomer in the polymer must be increased in these embodiments.

Sealant Formulation

Sealants according to the present disclosure include a polythioether according to the present disclosure and a curative. In some embodiments, the polythioether and curative are present in two separate components of a two-component or multi-component system. In some embodiments, the polythioether and curative are present in the same composition. In use, the polythioether and curative are mixed prior to cure of the sealant to form a seal.

In some embodiments, the curing agent is a crosslinking agent. In some embodiments, the curing agent comprises a polyepoxide, typically in embodiments where the polythioether polymer is a thiol-terminated polymer. Any suitable polyepoxide may be used, include those described above.

Adhesive Compositions

The polythioether according to the present disclosure may also be employed in adhesive compositions. In some embodiments the adhesive compositions may be one part epoxy adhesive compositions. Such compositions may demonstrate one or more advantages such as several days of shelf stability (stable viscosity), increased elongation, improved drop/shock resistance, and a desirable cure cycle (e.g., 65 C for 15 minutes). These characteristics are desirable in many application areas including electronics such as, for example, mobile handheld devices.

Selected Embodiments

The following embodiments, designated by letter and number, are intended to further illustrate the present disclosure but should not be construed to unduly limit this disclosure.

M1. A compound according to formula I:

$CH_2$=$CR^1$—$CHR^2$—S—$R^3$—S—$CHR^4$—$CR^5$=$CH_2$ [I]

wherein $R^1$, $R^2$, $R^4$ and $R^5$ are independently selected from —H, —$CH_3$ or —$C_2H_5$, and
wherein $R^3$ is selected from divalent groups comprising 2-12 carbon atoms, 0-5 ether oxygen atoms and 0-5 thioether sulfur atoms, which may be straight, branched or cyclic.

M2. The compound according to embodiment M1 wherein $R^1$ and $R^5$ are the same and $R^2$ and $R^4$ are the same.

M3. The compound according to embodiment M1 wherein $R^1$, $R^2$, $R^4$ and $R^5$ are independently selected from —H, or —$CH_3$.

M4. The compound according to embodiment M1 wherein one of $R^1$ and $R^2$ is —H and the other is —$CH_3$ and wherein one of $R^4$ and $R^5$ is —H and the other is —$CH_3$.

M5. The compound according to embodiment M1 wherein $R^1$ and $R^5$ are —$CH_3$ and $R^2$ and $R^4$ are —H.

M6. The compound according to embodiment M1 wherein $R^1$ and $R^5$ are —H and $R^2$ and $R^4$ are —$CH_3$.

M7. The compound according to embodiment M1 wherein $R^1$, $R^2$, $R^4$ and $R^5$ are —H.

M8. The compound according to any of embodiments M1-M7 wherein $R^3$ is a divalent group according to formula II:

$$-((CH_2)_n-X)_m-(CH_2)_n- \quad [II]$$

wherein m is 0-5,
wherein each n is independently selected from 2-6, and
wherein each X is independently selected from O or S.

M9. The compound according to any of embodiments M1-M7 wherein $R^3$ is a divalent group according to formula III:

$$-(C_2H_4-X)_m-C_2H_4- \quad [III]$$

wherein m is 0-5, and
wherein each X is independently selected from O or S.

M10. The compound according to any of embodiments M8-M9 wherein X is O.

M11. The compound according to any of embodiments M8-M9 wherein X is S.

M12. The compound according to any of embodiments M8-M11 wherein m is 1-5.

M13. The compound according to any of embodiments M8-M11 wherein m is 1-4.

M14. The compound according to any of embodiments M8-M11 wherein m is 1-3.

M15. The compound according to any of embodiments M8-M11 wherein m is 2.

M16. The compound according to any of embodiments M8-M11 wherein m is 1.

M17. The compound according to any of embodiments M1-M7 wherein $R^3$ is a divalent group according to formula IV:

$$-C_2H_4-O-C_2H_4-O-C_2H_4- \quad [IV].$$

M18. The compound according to any of embodiments M1-M7 wherein $R^3$ is a divalent group according to formula V:

$$-C_2H_4-S-C_2H_4- \quad [V].$$

PA1. A polythioether polymer which is a copolymer of one or more compounds according to any of embodiments M1-M15 with one or more polythiols.

PA2. A polythioether polymer which is a copolymer of one or more compounds according to any of embodiments M1-M15 with one or more polythiols and one or more polyepoxides.

PA3. The polythioether polymer according to embodiment PA2 wherein the one or more polyepoxides are aromatic.

PA4. The polythioether polymer according to embodiment PA2 wherein the one or more polyepoxides are according to formula XXX:

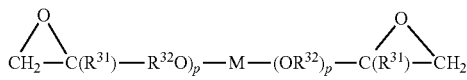

wherein M is selected from C2-10 alkyl groups, C6-20 aryl groups, and C6-20 aryl groups substituted with at least one C1-8 alkyl group or a N or O heteroatom;
wherein $R^{31}$ is selected from hydrogen or C1-C4 alkyl groups;
wherein $R^{32}$ is selected from divalent groups comprising 1-12 carbon atoms, 0-5 ether oxygen atoms and 0-5 thioether sulfur atoms, which may be straight, branched or cyclic; and
wherein P is 1-10.

PA5. The polythioether polymer according to embodiment PA4 wherein M is $-Ph-C(R^{33})_2-Ph-$, wherein $R^{33}$ is hydrogen or methyl.

PA6. The polythioether polymer according to any of embodiments PA1-PA5 wherein the polythiol is a dithiol according to formula VI:

$$HS-R^6-SH \quad [VI]$$

wherein $R^6$ is selected from divalent groups comprising 2-12 carbon atoms, 0-5 ether oxygen atoms and 0-5 thioether sulfur atoms, which may be straight, branched or cyclic.

PA7. The polythioether polymer according to embodiment PA6 wherein $R^6$ is the same group as $R^3$.

PA8. The polythioether polymer according to embodiment PA6 wherein $R^6$ is a divalent group according to formula II:

$$-((CH_2)_n-X)_m-(CH_2)_n- \quad [II]$$

wherein m is 0-5,
wherein each n is independently selected from 2-6, and
wherein each X is independently selected from O or S.

PA9. The polythioether polymer according to embodiment PA6 wherein $R^6$ is a divalent group according to formula III:

$$-(C_2H_4-X)_m-C_2H_4- \quad [III]$$

wherein m is 0-5, and
wherein each X is independently selected from O or S.

PA10. The polythioether polymer according to any of embodiments PA8-PA9 wherein X is O.

PA11. The polythioether polymer according to any of embodiments PA8-PA9 wherein X is S.

PA12. The polythioether polymer according to any of embodiments PA8-PA11 wherein m is 1-5.

PA13. The polythioether polymer according to any of embodiments PA8-PA11 wherein m is 1-4.

PA14. The polythioether polymer according to any of embodiments PA8-PA11 wherein m is 1-3.

PA15. The polythioether polymer according to any of embodiments PA8-PA11 wherein m is 2.

PA16. The polythioether polymer according to any of embodiments PA8-PA11 wherein m is 1.

PA17. The polythioether polymer according to embodiment PA6 wherein $R^6$ is a divalent group according to formula IV:

$$-C_2H_4-O-C_2H_4-O-C_2H_4- \quad [IV].$$

PA18. The polythioether polymer according to embodiment PA6 wherein $R^6$ is a divalent group according to formula V:

$$-C_2H_4-S-C_2H_4- \quad [V].$$

PA19. The polythioether polymer according to any of embodiments PA1-PA18 which is a thiol-terminated polymer.

PA20. The polythioether polymer according to any of embodiments PA1-PA18 which is a vinyl-terminated polymer.

PA21. The polythioether polymer according to any of embodiments PA1-PA20 comprising stabilizing units which are segments derived from monomers which are compounds according to any of embodiments M1-M15, wherein said stabilizing units comprise greater than 0.1 weight % of the polymer.

PA22. The polythioether polymer according to embodiment PA21, wherein said stabilizing units comprise greater than 0.6 weight % of the polymer.

PA23. The polythioether polymer according to embodiment PA21, wherein said stabilizing units comprise greater than 1.1 weight % of the polymer.

PA24. The polythioether polymer according to embodiment PA21, wherein said stabilizing units comprise greater than 3.1 weight % of the polymer.
PA25. The polythioether polymer according to embodiment PA21, wherein said stabilizing units comprise greater than 4.5 weight % of the polymer.
PA26. The polythioether polymer according to embodiment PA21, wherein said stabilizing units comprise greater than 6.1 weight % of the polymer.
PA27. The polythioether polymer according to any of embodiments PA1-PA24 comprising stabilizing units which are segments derived from monomers which are compounds according to any of embodiments M1-M15, wherein said stabilizing units comprise less than 30 weight % of the polymer.
PA28. The polythioether polymer according to embodiment PA27, wherein said stabilizing units comprise less than 24 weight % of the polymer.
PA29. The polythioether polymer according to embodiment PA27, wherein said stabilizing units comprise less than 15 weight % of the polymer.
PA30. The polythioether polymer according to embodiment PA27, wherein said stabilizing units comprise less than 9.5 weight % of the polymer.
PA31. The polythioether polymer according to embodiment PA27, wherein said stabilizing units comprise less than 8.5 weight % of the polymer.
PA32. The polythioether polymer according to embodiment PA27, wherein said stabilizing units comprise less than 7.5 weight % of the polymer.
PA33. The polythioether polymer according to embodiment PA27, wherein said stabilizing units comprise less than 6.5 weight % of the polymer.
PA34. The polythioether polymer according to embodiment PA27, wherein said stabilizing units comprise less than 4.5 weight % of the polymer.
PA35. The polythioether polymer according to any of embodiments PA1-PA32 comprising epoxy units which are segments derived from polyepoxides wherein said epoxy units comprise greater than 0.1 weight % of the polymer.
PA36. The polythioether polymer according to embodiment PA35, wherein said epoxy units comprise greater than 0.6 weight % of the polymer.
PA37. The polythioether polymer according to embodiment PA35, wherein said epoxy units comprise greater than 1.1 weight % of the polymer.
PA38. The polythioether polymer according to embodiment PA35, wherein said epoxy units comprise greater than 3.1 weight % of the polymer.
PA39. The polythioether polymer according to any of embodiments PA1-PA38 comprising epoxy units which are segments derived from polyepoxides, wherein said epoxy units comprise less than 20 weight % of the polymer.
PA40. The polythioether polymer according to embodiment PA39, wherein said epoxy units comprise less than 9.5 weight % of the polymer.
PA41. The polythioether polymer according to embodiment PA39, wherein said epoxy units comprise less than 6 weight % of the polymer.
PA42. The polythioether polymer according to any of embodiments PA1-PA41 derived from a reaction mixture comprising a molar excess of polythiols over other reactive species of greater than 101/99.
PA43. The polythioether polymer according to any of embodiments PA1-PA41 derived from a reaction mixture comprising a molar excess of polythiols over other reactive species of greater than 102/98.
PA44. The polythioether polymer according to any of embodiments PA1-PA41 derived from a reaction mixture comprising a molar excess of polythiols over other reactive species of greater than 103/97.
PA45. The polythioether polymer according to any of embodiments PA1-PA41 derived from a reaction mixture comprising a molar excess of polythiols over other reactive species of greater than 104/96.
PB1. A polythioether polymer comprising divalent groups in the polymer backbone according to formula XI:

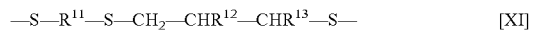
$$—S—R^{11}—S—CH_2—CHR^{12}—CHR^{13}—S— \quad [XI]$$

wherein $R^{11}$ is selected from divalent groups comprising 2-12 carbon atoms, 0-5 ether oxygen atoms and 0-5 thioether sulfur atoms, which may be straight, branched or cyclic; and wherein $R^{12}$ and $R^{13}$ are independently selected from —H, —$CH_3$ or —$C_2H_5$, provided that at least one of $R^{12}$ and $R^{13}$ is not —H.
PB2. The polythioether polymer according to embodiments PB1 comprising divalent groups in the polymer backbone according to formula XII:

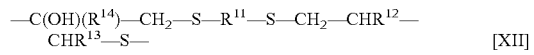
$$—C(OH)(R^{14})—CH_2—S—R^{11}—S—CH_2—CHR^{12}—CHR^{13}—S— \quad [XII]$$

wherein $R^{14}$ is selected from —H or $C_{1-4}$ alkyl; and wherein $R^{11}$, $R^{12}$ and $R^{13}$ are as defined above.
PB3. The polythioether polymer according to embodiment PB2 wherein $R^{14}$ is selected from —H or $CH_3$.
PB4. The polythioether polymer according to embodiment PB2 wherein $R^{14}$ is —H.
PB5. The polythioether polymer according to any of embodiments PB1-PB4 comprising divalent groups in the polymer backbone according to formula XIII:

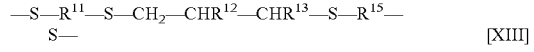
$$—S—R^{11}—S—CH_2—CHR^{12}—CHR^{13}—S—R^{15}—S— \quad [XIII]$$

wherein $R^{15}$ is selected from divalent groups comprising 2-12 carbon atoms, 0-5 ether oxygen atoms and 0-5 thioether sulfur atoms, which may be straight, branched or cyclic; and wherein $R^{11}$, $R^{12}$ and $R^{13}$ are as defined above.
PB6. The polythioether polymer according to embodiment PB5 wherein $R^{15}$ is the same group as $R^{11}$.
PB7. The polythioether polymer according to any of embodiments PB1-PB6 additionally comprising divalent groups in the polymer backbone according to formula XIV:

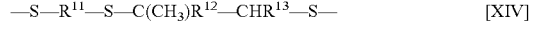
$$—S—R^{11}—S—C(CH_3)R^{12}—CHR^{13}—S— \quad [XIV]$$

wherein $R^{11}$, $R^{12}$ and $R^{13}$ are as defined above.
PB8. The polythioether polymer according to any of embodiments PB1-PB7 wherein $R^{12}$ and $R^{13}$ are independently selected from —H, or —$CH_3$.
PB9. The polythioether polymer according to any of embodiments PB1-PB7 wherein $R^{12}$ is —$CH_3$ and $R^{13}$ is —H.
PB10. The polythioether polymer according to any of embodiments PB1-PB7 wherein $R^{12}$ is —H and $R^{13}$ is —$CH_3$.
PB11. The polythioether polymer according to any of embodiments PB1-PB10 wherein $R^{11}$ is a divalent group according to formula II:

$$—((CH_2)_n—X)_m—(CH_2)_n— \quad [II]$$

wherein m is 0-5,
wherein each n is independently selected from 2-6, and
wherein each X is independently selected from O or S.

PB12. The polythioether polymer according to any of embodiments PB1-PB10 wherein $R^H$ is a divalent group according to formula III:

$$-(C_2H_4-X)_m-C_2H_4- \quad [III]$$

wherein m is 0-5, and
wherein each X is independently selected from O or S.
PB13. The polythioether polymer according to any of embodiments PB11-PB12 wherein X is O.
PB14. The polythioether polymer according to any of embodiments PB11-PB12 wherein X is S.
PB15. The polythioether polymer according to any of embodiments PB11-PB14 wherein m is 1-5.
PB16. The polythioether polymer according to any of embodiments PB11-PB14 wherein m is 1-4.
PB17. The polythioether polymer according to any of embodiments PB11-PB14 wherein m is 1-3.
PB18. The polythioether polymer according to any of embodiments PB11-PB14 wherein m is 2.
PB19. The polythioether polymer according to any of embodiments PB11-PB14 wherein m is 1.
PB20. The polythioether polymer according to any of embodiments PB1-PB10 wherein $R^{11}$ is a divalent group according to formula IV:

$$-C_2H_4-O-C_2H_4-O-C_2H_4- \quad [IV].$$

PB21. The polythioether polymer according to any of embodiments PB1-PB10 wherein $R^{11}$ is a divalent group according to formula V:

$$-C_2H_4-S-C_2H_4- \quad [V].$$

PB22. The polythioether polymer according to any of embodiments PB1-PB21 which is a thiol-terminated polymer
PB23. The polythioether polymer according to any of embodiments PB1-PB21 which is a vinyl-terminated polymer.
PC1. A polythioether polymer comprising divalent groups in the polymer backbone according to formula XXI:

$$-S-R^{21}-S-CH(CH_3)-CH_2-S- \quad [XXI]$$

wherein $R^{21}$ is selected from divalent groups comprising 2-12 carbon atoms, 0-5 ether oxygen atoms and 0-5 thioether sulfur atoms, which may be straight, branched or cyclic.
PC2. The polythioether polymer according to embodiments PC1 comprising divalent groups in the polymer backbone according to formula XXII:

$$-C(OH)(R^{22})-CH_2-S-R^{21}-S-CH(CH_3)-CH_2-S- \quad [XXII]$$

wherein $R^{22}$ is selected from —H or C1-4 alkyl; and
wherein $R^{21}$ is as defined above.
PC3. The polythioether polymer according to embodiment PC2 wherein $R^{22}$ is selected from —H or $CH_3$.
PC4. The polythioether polymer according to embodiment PC2 wherein $R^{22}$ is —H.
PC5. The polythioether polymer according to any of embodiments PC1-PC4 comprising divalent groups in the polymer backbone according to formula XXIII:

$$-S-R^{21}-S-CH(CH_3)-CH_2-S-R^{23}-S- \quad [XXIII]$$

wherein $R^{23}$ is selected from divalent groups comprising 2-12 carbon atoms, 0-5 ether oxygen atoms and 0-5 thioether sulfur atoms, which may be straight, branched or cyclic; and
wherein $R^{21}$ is as defined above.
PC6. The polythioether polymer according to embodiment PC5 wherein $R^{23}$ is the same group as $R^{21}$.
PC7. The polythioether polymer according to any of embodiments PC1-PC6 wherein $R^{21}$ is a divalent group according to formula II:

$$-((CH_2)_n-X)_m-(CH_2)_n- \quad [II]$$

wherein m is 0-5,
wherein each n is independently selected from 2-6, and
wherein each X is independently selected from O or S.
PC8. The polythioether polymer according to any of embodiments PC1-PC6 wherein $R^{21}$ is a divalent group according to formula III:

$$-(C_2H_4-X)_m-C_2H_4- \quad [III]$$

wherein m is 0-5, and
wherein each X is independently selected from O or S.
PC9. The polythioether polymer according to any of embodiments PC7-PC8 wherein X is O.
PC10. The polythioether polymer according to any of embodiments PC7-PC8 wherein X is S.
PC11. The polythioether polymer according to any of embodiments PC7-PC10 wherein m is 1-5.
PC12. The polythioether polymer according to any of embodiments PC7-PC10 wherein m is 1-4.
PC13. The polythioether polymer according to any of embodiments PC7-PC10 wherein m is 1-3.
PC14. The polythioether polymer according to any of embodiments PC7-PC10 wherein m is 2.
PC15. The polythioether polymer according to any of embodiments PC7-PC10 wherein m is 1.
PC16. The polythioether polymer according to any of embodiments PC1-PC6 wherein $R^{2'}$ is a divalent group according to formula IV:

$$-C_2H_4-O-C_2H_4-O-C_2H_4- \quad [IV].$$

PC17. The polythioether polymer according to any of embodiments PC1-PC6 wherein $R^{2'}$ is a divalent group according to formula V:

$$-C_2H_4-S-C_2H_4- \quad [V].$$

PC18. The polythioether polymer according to any of embodiments PC1-PA17 which is a thiol-terminated polymer.
PC19. The polythioether polymer according to any of embodiments PC1-PC17 which is a vinyl-terminated polymer.
S1. A sealant comprising:
  a) the polythioether polymer according to any of embodiments PA1-PA45, PB1-PB23 or PC1-PC19; and
  b) a curing agent.
S2. The sealant according to embodiment S1 wherein the curing agent is a crosslinking agent.
S3. The sealant according to embodiment S1 wherein the curing agent comprises a polyepoxide.
S4. The sealant according to embodiment S1 wherein the polythioether polymer is a thiol-terminated polymer and the curing agent comprises a polyepoxide.
S5. The sealant according to embodiment S1 wherein the curing agent comprises an aromatic polyepoxide.
S6. The sealant according to embodiment S1 wherein the polythioether polymer is a thiol-terminated polymer and the curing agent comprises an aromatic polyepoxide.
CS1. A material obtained by curing a sealant according to any of embodiments S1-56.

Objects and advantages of this disclosure are further illustrated by the following examples, but the particular materials and amounts thereof recited in these examples, as well as other conditions and details, should not be construed to unduly limit this disclosure.

EXAMPLES

Unless otherwise noted, all reagents were obtained or are available from Sigma-Aldrich Company, St. Louis, Mo., or may be synthesized by known methods. Unless otherwise reported, all ratios are by weight percent.
The following abbreviations are used to describe the examples:
- °C.: degrees Centigrade
- °F.: degrees Fahrenheit
- cm: centimeter
- Kg-lcm: kilograms per linear centimeter
- kPa: kiloPascals
- MW: molecular weight
- mL: milliliter
- mm: millimeter
- p-li: pounds per linear inch
- psi: pounds per square inch
- $T_g$: glass transition temperature Materials.
Abbreviations for the materials used in the examples are as follows:
- A-187: gamma-glycidoxypropyltrimethoxysilane, obtained under the trade designation "SILQUEST A187" from Momentive, Columbus, Ohio.
- AC-160: A water-based adhesion promoter, obtained under the trade designation "ADHESION PROMOTER AC-160" from 3M Company, St. Paul, Minn.
- CB: 3-chloro-1-butene.
- CB-R410: A carbon black pigment, obtained under the trade designation "RAVEN 410" from Columbia Chemicals, Marietta, Ga.
- CMP: 3-chloro-2-methyl-1-propene.
- DABCO: Triethylenediamine, obtained under the trade designation "DABCO" from Air Products & Chemicals, Inc., Allentown, Pa.
- DABCO-33LV: A solution of 33% triethylenediamine and 67% dipropylene glycol, obtained under the trade designation "DABCO-33LV" from Air Products & Chemicals, Inc.
- DMDO: 1,8-Dimercapto-3,6-dioxaoctane, obtained from Arkema, Inc., King of Prussia, Pa.
- DMDO-AC Diene: 4,13-dithia-7,10-dioxa-hexadecyl-1,15-diene, a stabilizing diene made as described in Monomer Example 2, below.
- DMDO-CMP Diene: 4,13-dithia-7,10-dioxa-2,15-dimethyl-hexadecyl-1,15-diene, a stabilizing diene made as described in Monomer Example 1, below.
- DMDS: bis(2-mercaptoethyl) sulfide, obtained from Nisso/YSK, Japan.
- DMDS-CMP Diene: 4,7,10-trithia-2,12-dimethyldodeca-1,12-diene, a stabilizing diene made as described in Monomer Example 3, below.
- DVE-3: Triethyleneglycol divinylether, obtained under the trade designation "RAPI-CURE DVE-3" from Ashland Specialty Ingredients, Wilmington, Del.
- E-8220: A diglycidylether of bisphenol F, obtained under the trade designation "EPALLOY 8220" from Emerald Performance Materials, LLC, Cuyahoga Falls, Ohio.
- JRF1: Jet Reference Fluid Type 1 composition, as defined by SAE Standard AMS2629, obtained from Chevron-Phillips, The Woodlands, Tex.
- NCC: Nanoparticle calcium carbonate, obtained under the trade designation "SOCAL 322" from Solvay Chemicals, Inc., Houston, Tex.
- PSB: calcium carbonate, obtained under the trade designation "Polcarb SB" from Imerys Performance & Filtration Minerals, Cornwall, U.K.
- R-202: A surface modified fumed silica, obtained under the trade designation "AEROSIL R202" from Evonik Industries, AG, Essen, Germany.
- Talc: A talc, obtained under the trade designation "TALCRON MP10-52" from Specialty Minerals, Bethlehem, Pa.
- TC-300: A precipitated calcium carbonate, obtained under the trade designation "THIXOCARB 300" from Specialty Minerals.
- TMP-TGE: Trimethylolpropane triglycidylether, obtained under the trade designation "ERISYS GE-30" from Emerald Performance Materials Company.
- TP-R900: Titanium dioxide, obtained under the trade designation "TIPURE R900" from E.I. du DuPont de Nemours and Company, Wilmington, Del.
- TVCH: 1,2,4-Trivinylcyclohexane, obtained from BASF Corp., Florham Park, N.J.
- ULTRA-PFLEX: A precipitated calcium carbonate, obtained under "ULTRA-PFLEX" from Specialty Minerals.
- VAZO 52: 2,2'-azobis(2,4-dimethyl-pentanenitrile), obtained under the trade designation "VAZO 52" from E.I. du DuPont de Nemours and Company.
- VAZO 67: 2,2'azobis-(2-methylbutyronitrile), obtained under the trade designation "VAZO 67" from E.I. du DuPont de Nemours and Company.

MONOMER EXAMPLES

Monomer examples of the present disclosure were prepared as follows, with the exception of monomer example 4, which is prophetic.

Monomer Example 1

Synthesis of 4,13-dithia-7,10-dioxa-2,15-dimethyl-hexadecyl-1,15-diene (DMDO-CMP Diene)

Into a 500 mL four-neck, round bottom flask fitted with a stirrer, thermometer, chilled water condenser and a pressure equalizing addition funnel was added 206.54 grams of a 20% aqueous solution of sodium hydroxide (1.033 moles). To this was added, drop wise with stirring, 94.08 grams (0.51 moles) DMDO, and the mixture then allowed to cool to approximately 21° C. 96.4 grams (1.065 moles) CMP was added drop wise with vigorous stirring, and stirring continued for another 2 hours. The mixture was then held at 21° C. for approximately 16 hours, after which 150 grams of a clear layer was decanted. NMR analysis confirmed the decanted layer to be CMP diene.

Monomer Example 2

Synthesis of 4,13-dithia-7,10-dioxa-hexadecyl-1,15-diene (DMDO AC Diene)

114.4 grams of a 20% aqueous solution of sodium hydroxide (0.57 moles) were added to a 250 mL round bottomed flask fitted with a stirrer, chilled water condenser, a pressure equalizing funnel, thermometer, and nitrogen line. After the flask was flushed with nitrogen, 52.1 grams DMDO (0.29 moles) were added dropwise while stirring, and the mixture allowed to cool to approximately 21° C. 45.1 grams allyl chloride (0.57 moles) were slowly added to the flask while stirring, and stirring continued for several hours. The mixture was then allowed to stand for several more hours. The top layer was removed and stripped on a rotary evaporator at approximately 70° C. for 10 minutes. Approximately 65 grams of material was obtained.

Monomer Example 3

Synthesis of
4,7,10-trithia-2,12-dimethyldodeca-1,12-diene
(DMDS-CMP Diene)

Into a 500 mL four-neck, round bottom flask fitted with a stirrer, thermometer, chilled water condenser and a pressure equalizing addition funnel was added 206.54 grams of a 20% aqueous solution of sodium hydroxide (1.033 moles). To this was added, drop wise with stirring, 78.7 grams (0.51 moles) DMDS, and the mixture then allowed to cool to approximately 21° C. 96.4 grams (1.065 moles) CMP was added drop wise with vigorous stirring, and stirring continued for another 2 hours. The mixture was then held at 21° C. for approximately 16 hours, after which 140 grams of a clear layer was decanted.

Monomer Example 4 (Prophetic)

Synthesis of 4, 13-dithia-7,10-dioxa-3,
14-dimethylhexadecyl-1,15-diene (DMDO-CB
Diene)

Into a 500 mL four-neck, round bottom flask fitted with a stirrer, thermometer, chilled water condenser and a pressure equalizing addition funnel is added 206.54 grams of a 20% aqueous solution of sodium hydroxide (1.033 moles). To this is added, drop wise with stirring, 94.08 grams (0.51 moles) DMDO, and the mixture is then allowed to cool to approximately 21° C. 96.4 grams (1.065 moles) CB is added drop wise with vigorous stirring, and stirring is continued for another 3 hours. The mixture is then held at 21° C. for approximately 24 hours, after which a clear layer of product is decanted.

POLYTHIOETHER EXAMPLES

Polythioether examples of the present disclosure were prepared as follows.

Polythioether Example 1

Into a 100-mL round bottom flask equipped with an air-driven stirrer, thermometer, and a dropping funnel, was added 39.64 grams (0.22 moles) DMDO and 4.10 grams (0.0125 moles) E-8220. To this mixture was added 0.02 grams DABCO The system was flushed with nitrogen, then mixed and heated for 1.5 hours at 60-70° C. 8.89 grams (0.034 moles) DMDO-CMP Diene was added followed by approximately 0.01 grams VAZO 52. With continuous stirring, the mixture was maintained at 60° C. for approximately 1.5 hrs. 0.83 grams (0.005 mole) TVCH were added and the temperature maintained for another 1.5 hrs. 31.80 grams (0.157 moles) DVE-3 were slowly added drop-wise to the flask over a period of 45-60 minutes, keeping the temperature at approximately 70° C. Additional VAZO 52 was added in approximately 0.01 gram increments over approximately 16 hours, for a total amount of about 0.4 grams. The temperature is raised to 100° C. and the material degassed for approximately 10 minutes. The resultant polythioether was approximately 3200 MW with a 2.2 functionality.

Polythioether Example 2

Into a 250-mL round bottom flask equipped with an air-driven stirrer, thermometer, and a dropping funnel, was added 99.48 grams (0.55 moles) DMDO and 10.24 grams (0.03 moles) E-8220. To this mixture was added 0.04 grams DABCO. The system was flushed with nitrogen, then mixed and heated for 1.5 hours at 60-70° C. 3.66 grams (0.0125 moles) DMDO-AC Diene was added, followed by approximately 0.03 grams VAZO 52. With continuous stirring, the mixture was maintained at 60° C. for approximately 1.5 hrs. 2.00 grams (0.012 mole) TVCH were added and the temperature maintained for another 1.5 hrs. 79.42 grams (0.39 moles) DVE-3 were slowly added drop-wise to the flask over a period of 45-60 minutes, keeping the temperature at approximately 70° C. Additional VAZO 52 was added in approximately 0.03 gram increments over approximately 16 hours, for a total amount of about 0.6 grams. The temperature was raised to 100° C. and the material degassed for approximately 10 minutes. The resultant polythioether was approximately 3200 MW with a 2.2 functionality.

Polythioether Comparative A

A comparative polythioether was prepared according to the general procedure described in Polythioether Example 1, wherein DMDO-CMP Diene was omitted and the following amounts of E-8220 and DVE-3 increased to 4.16 grams (0.013 moles) and 34.91 grams (0.173 moles), respectively.

Polythioether Example 3

Into a 100-mL round bottom flask equipped with an air-driven stirrer, thermometer, and a dropping funnel, was added 36.68 grams (0.20 moles) DMDO and 4.17 grams (0.0127 moles) E-8220. To this mixture was added 0.02 grams DABCO. The system was flushed with nitrogen, then mixed and heated for 1.5 hours at 60-70° C. 23.92 grams (0.082 moles) DMDO-CMP Diene was added, followed by approximately 0.01 grams VAZO 52. With continuous stirring, an additional 0.13 grams VAZO 52 was added, the mixture maintained at 60° C. for another 4.5 hrs. 0.81 grams (0.005 moles) TVCH was then added, along with an additional 0.02 grams VAZO 52, and maintained at 60° C. for another 1.5 hrs. 14.44 grams (0.07 moles) DVE-3 was then added drop-wise to the flask over 15 minutes, keeping the temperature at approximately 70° C. Additional VAZO 52 was added in approximately 0.01 gram increments over approximately 16 hours for a total of about 0.4 grams. The temperature was raised to 100° C. and the material degassed for approximately 10 minutes. The resultant polythioether was approximately 3200 MW with 2.2 functionality.

Polythioether Example 4

Into a 100-mL round bottom flask equipped with an air-driven stirrer, thermometer, and a dropping funnel, was added 39.78 grams (0.216 moles) DMDO and 4.15 grams (0.013 moles) E-8220. To this mixture was added 0.02 grams DABCO. The system was flushed with nitrogen, then mixed and heated for 1.5 hours at 60-70° C. 3.28 grams (0.012 moles) DMDS-CMP Diene was added, followed by approximately 0.01 gram VAZO 52. With continuous stirring, 0.81 grams (0.005 moles) TVCH and an additional 0.13 grams VAZO 52 were added, the mixture then heated to 60° C., and held at this temperature for another 1.5 hrs. 31.98 grams (0.158 moles) DVE-3 was then added drop-wise to the flask over 45-60 minutes, while maintaining the temperature at approximately 70° C. Additional VAZO 52 was added in approximately 0.01 gram increments over approximately 16 hours for a total of about 0.4 grams. The temperature was raised to 100° C. and the material degassed for approximately 10 minutes. The resultant polythioether was approximately 3200 MW with 2.2 functionality.

Polythioether Example 5

The procedure generally described for synthesizing Polythioether Example 4 was repeated, wherein the quantity of DMDS-CMP Diene was doubled to 6.56 grams (0.025 moles), and the amounts of DMDO and DVE-3 were 39.42 and 29.06 grams, respectively. The resultant polythioether was approximately 3200 MW with 2.2 functionality.

Polythioether Example 6

A polythioether was prepared according to the procedure generally described in Polythioether Example 1, wherein both the epoxy and the amine were omitted. The amount of DMDO-CMP Diene was 4.6% by weight.

Polythioether Example 7

A polythioether was prepared according to the procedure generally described in Polythioether Example 2, wherein both the epoxy and the amine were omitted. The amount of DMDO-AC Diene was 4.1% by weight.

Polythioether Example 8

An olefin-terminated polythioether example of the present disclosure was prepared as follows. Into a 100-mL round bottom flask equipped with an air-driven stirrer, thermometer, and a dropping funnel, was added 171.93 grams (0.94 moles) DMDO and 20.52 grams (0.06 moles) E-8220. To this mixture was added 0.10 grams DABCO. The system was flushed with nitrogen, then mixed and heated for 1.5 hours at 60-70° C. 18.15 grams (0.6 moles) DMDO-CMP Diene was added, followed by approximately 0.10 gram VAZO 52. With continuous stirring, 4.09 grams (0.025 moles) TVCH was added and the mixture maintained for another 1.5 hours at 60° C. 185.54 grams (0.0.92 moles) DVE-3 was then added drop-wise to the flask over 45-60 minutes, while maintaining the temperature at approximately 70° C. Additional VAZO 52 was added in approximately 0.1 gram increments over approximately 16 hours for a total of about 0.6 grams. The temperature was raised to 100° C. and the material degassed for approximately 10 minutes. The resultant polythioether was approximately 3200 MW with 2.2 functionality.

Polythioether Example 9

A polythioether of the present disclosure was prepared according to the general procedure described in Polythioether Example 6, wherein the amount of DMDO-CMP Diene was increased from 4.6 to 9.1 wt. % and DVE-3 was reduced from 44.0 to 40.10 wt. %.

Polythioether Example 10

A polythioether of the present disclosure was prepared according to the general procedure described in Polythioether Example 7, wherein the amount of Polythioether Example 2 was increased from 4.1 to 9.1 wt. % and DVE-3 was reduced from 44.2 to 39.8 wt. %.

Crystallization Evaluation

Small glass vials of selected polythioether examples and comparatives were placed in a temperature controlled room at 40° F. (4.4° C.) and monitored weekly for the formation of solids. The degree of polythioether crystallization was subjectively recorded as the volume of solids formation in the vial, in increments of 5%. Results are listed in Table 1.

TABLE 1

| Poly-thioether | Stabilizing Diene | | Epoxy (Wt. %) | Tg (° C.) | Polythioether Crystallization | |
|---|---|---|---|---|---|---|
| | Type | Wt. % | | | Volume (%) | Time (Days) |
| Example 1 | DMDO-CMP | 4.5 | 5.2 | −56.2 | 0 | 189 |
| Example 2 | DMDO-AC | 4.4 | 5.2 | −56.9 | 10 | 49 |
| Example 3 | DMDO-CMP | 29.9 | 5.2 | N/M* | 0 | 238 |
| Example 4 | DMDS-CMP | 4.1 | 5.2 | −56.7 | 0 | 182 |
| Example 5 | DMDS-CMP | 8.2 | 5.2 | −56.3 | 0 | 182 |
| Example 6 | DMDO-CMP | 4.6 | 0 | −57.4 | 10 | 91 |
| Example 7 | DMDO-AC | 4.1 | 0 | −58.4 | 20 | 14 |
| Example 9 | DMDO-CMP | 9.1 | 0 | −59.5 | 0 | 224 |
| Example 10 | DMDO-AC | 9.1 | 0 | −60.2 | 0 | 224 |
| Comparative A | None | 0 | 5.2 | −58 | 10 | 28 |

SEALANT EXAMPLES

Sealant Example 1

A filled polythioether of the present disclosure was prepared as follows. 36 grams of Polythioether Example 1 was mixed with 24 grams PSB and cured with an 80:20 by weight blend of E-8220 and TMP-TGE, using 0.36 grams DABCO 33LV as a catalyst. After curing for 16 hours at 21° C., the sample was transferred to an oven, set at 140° F. (60° C.), for two hours to ensure completeness of cure.

Sealant Example 2

A filled polythioether of the present disclosure was prepared and cured according to the process generally described in Polythioether Example 6, wherein Polymer Example 1 was replaced with an equal amount of Polymer Example 2.

Sealant Comparative B

A comparative filled polythioether was prepared and cured according to the procedure generally described in Polymer Example 6, wherein Polythioether Example 1 was replaced with an equal amount of Comparative Polymer A.

Cured filled polythioether Examples 6-7 and polythioether Comparative B were immersed in Jet Reference Fluid Type 1 (JRF1), as defined by SAE Standard AMS2629, for 7 days at 60° C., after which % swell and % weight gain of the sample were determined. Jet Fuel Resistance data and physical properties are listed in Table 2.

TABLE 2

| Sealant | Stabilizing Diene Type | Wt. % | Epoxy (Wt. %) | Physical Properties | | | Jet Fuel Resistance | |
|---|---|---|---|---|---|---|---|---|
| | | | | Tensile Strength (psi/kPa) | Elongation at Break (%) | Tear Strength (p-li/kg-lcm) | % Swell in JRF1 | % Swell in Deionized Water |
| Comparative B | None | 0 | 5.2 | 290/2,000 | 317 | 48.0/8.57 | 13.6 | 8.1 |
| Example 1 | DMDO-CMP | 4.5 | 5.2 | 331/2,281 | 434 | 47.0/8.40 | 17.5 | 5.2 |
| Example 2 | DMDO-AC | 4.4 | 5.2 | 383/2,641 | 506 | 49.0/8.75 | 18.1 | 5.2 |

Sealant Examples 3-5

Additional examples of sealants according to the present disclosure were prepared as follows. Base and catalyst compositions were prepared by manually mixing, at 21° C., the components in the amounts and in the sequences listed in Tables 3A and 3B.

TABLE 3A

| | Sealant Base (grams) | |
|---|---|---|
| Component | SB-1 | SB-2 |
| Polythioether Example 1 | 100.0 | 60.0 |
| TP-R900 | 1.0 | 0 |
| NCC | 40.0 | 22.4 |
| TC-300 | 5.0 | 0 |
| R-202 | 1.5 | 0 |
| DABCO 33LV | 0.6 | 0.5 |
| Talc | 0 | 8.0 |

TABLE 3B

| | Catalyst (grams) | |
|---|---|---|
| Component | C-1 | C-2 |
| E-8220 | 100.0 | 6.55 |
| TC-300 | 10.0 | 0 |
| ULTRA-PFLEX | 40.0 | 0 |
| CB-R410 | 0.5 | 0.25 |
| R-202 | 2.5 | 0 |
| A-187 | 10.0 | 1.0 |
| TMP-TGE | 0 | 0.35 |
| NCC | 0 | 0.94 |

Sealant Example 3

100 parts by weight Sealant Base SB-1 was mixed with 11.2 parts by weight Catalyst C-1, at 21° C., until homogeneous. The mixture was cured for approximately 16 hours at 21° C., then held in an oven set at 140° F. (60° C.) for two hours.

Sealant Example 4

100 parts by weight Sealant Base SB-1 was mixed with 11.2 parts by weight Catalyst C-1, at 21° C., until homogeneous. The mixture was cured for approximately 16 hours at 21° C., then held in an oven set at 140° F. (60° C.) for two hours, followed by another two hours at 420° F. (215.6° C.).

Sealant Example 5

100 parts by weight Sealant Base SB-2 was mixed with 10.0 parts by weight Catalyst C-2, at 21° C., until homogeneous. The mixture was cured for approximately 16 hours at 21° C., then held in an oven set at 140° F. (60° C.) for two hours.

With respect to Sealant Example 3, a sample of cured material was immersed in Jet Reference Fluid Type 1 (JRF1) for 7 days at 60° C., after which % swell and % weight gain of the sample were determined. JRF1 composition is defined by SAE Standard AMS2629. Swell was determined to be 17.6% in JRF1, versus 13.7% in deionized water.

Sealant Examples 3-5 exhibited good adhesion to aluminum panels coated with primer AMS-C-27725, using an adhesion promoter AC-160, obtained from 3M Company, (Sealant Examples 3-4) and without an adhesion promoter (Sealant Example 5). Tensile strength measurements are listed in Table 4.

TABLE 4

| Sealant Example | Tensile Strength (psi/kPa) | % Elongation at Break (%) |
|---|---|---|
| 3 | 375/2,586 | 293 |
| 4 | 223/1,538 | 272 |
| 5 | 418/2882 | 260 |

Various modifications and alterations of this disclosure will become apparent to those skilled in the art without departing from the scope and principles of this disclosure, and it should be understood that this disclosure is not to be unduly limited to the illustrative embodiments set forth hereinabove.

We claim:

1. A polythioether polymer which is a copolymer of one or more compounds according to formula I:

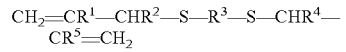

$$CH_2=CR^1—CHR^2—S—R^3—S—CHR^4—CR^5=CH_2 \quad [I]$$

wherein $R^1$, $R^2$, $R^4$ and $R^5$ are independently selected from —H, —$CH_3$ or —$C_2H_5$, and
wherein $R^3$ is selected from divalent groups comprising 2-12 carbon atoms, 0-5 ether oxygen atoms and 0-5 thioether sulfur atoms, which may be straight, branched or cyclic;
with one or more polythiols.

2. The polythioether polymer according to claim 1 wherein $R^1$ and $R^5$ are the same and are selected from —H and —$CH_3$ and wherein $R^2$ and $R^4$ are the same and are selected from —H and —$CH_3$.

3. The polythioether polymer according to claim 1 wherein $R^1$ and $R^5$ are —$CH_3$ and $R^2$ and $R^4$ are —H.

4. The polythioether polymer according to claim 1 wherein $R^3$ is a divalent group according to formula II:

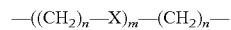

$$—((CH_2)_n—X)_m—(CH_2)_n— \quad [II]$$

wherein m is 0-5,
wherein each n is independently selected from 2-6, and
wherein each X is independently selected from O or S.

5. The polythioether polymer according to claim 1 which is a copolymer also with one or more polyepoxides.

6. The polythioether polymer according to claim 1 wherein the polythiol is a dithiol according to formula VI:

$$HS-R^6-SH \quad [VI]$$

wherein $R^6$ is selected from divalent groups comprising 2-12 carbon atoms, 0-5 ether oxygen atoms and 0-5 thioether sulfur atoms, which may be straight, branched or cyclic.

7. The polythioether polymer according to claim 6 wherein $R^6$ is the same group as $R^3$.

8. The polythioether polymer according to claim 6 wherein $R^6$ is a divalent group according to formula II:

$$-((CH_2)_n-X)_m-(CH_2)_n- \quad [II]$$

wherein m is 0-5,
wherein each n is independently selected from 2-6, and
wherein each X is independently selected from O or S.

9. The polythioether polymer according to claim 1 which is a thiol-terminated polymer.

10. The polythioether polymer according to claim 1 comprising stabilizing units which are segments derived from monomers which are compounds according to formula I, wherein said stabilizing units comprise greater than 1.1 weight % of the polymer and less than 24 weight % of the polymer.

11. The polythioether polymer according to claim 1 comprising epoxy units which are segments derived from polyepoxides wherein said epoxy units comprise greater than 1.1 weight % of the polymer and less than 20 weight % of the polymer.

12. The polythioether polymer according to claim 1 derived from a reaction mixture comprising a molar excess of polythiols over other reactive species of greater than 101/99.

13. A polythioether polymer comprising divalent groups in the polymer backbone according to formula XI:

$$-S-R^{11}-S-CH_2-CHR^{12}-CHR^{13}-S- \quad [XI]$$

wherein $R^{11}$ is selected from divalent groups comprising 2-12 carbon atoms, 0-5 ether oxygen atoms and 0-5 thioether sulfur atoms, which may be straight, branched or cyclic; and
wherein $R^{12}$ and $R^{13}$ are independently selected from $-H$, $-CH_3$ or $-C_2H_5$, provided that at least one of $R^{12}$ and $R^{13}$ is not $-H$.

14. The polythioether polymer according to claim 13 comprising divalent groups in the polymer backbone according to formula XII:

$$-C(OH)(R^{14})-CH_2-S-R^{11}-S-CH_2-CHR^{12}-CHR^{13}-S- \quad [XII]$$

wherein $R^{14}$ is selected from $-H$ or $C_{1-4}$ alkyl; and
wherein $R^{11}$, $R^{12}$ and $R^{13}$ are as defined above.

15. The polythioether polymer according to claim 13 comprising divalent groups in the polymer backbone according to formula XIII:

$$-S-R^{11}-S-CH_2-CHR^{12}-CHR^{13}-S-R^{15}-S- \quad [XIII]$$

wherein $R^{15}$ is selected from divalent groups comprising 2-12 carbon atoms, 0-5 ether oxygen atoms and 0-5 thioether sulfur atoms, which may be straight, branched or cyclic; and
wherein $R^{11}$, $R^{12}$ and $R^{13}$ are as defined above.

16. The polythioether polymer according to claim 15 wherein $R^{15}$ is the same group as $R^{11}$.

17. The polythioether polymer according to claim 13 wherein $R^{12}$ is $-CH_3$ and $R^{13}$ is $-H$.

18. The polythioether polymer according to claim 13 wherein $R^{11}$ is a divalent group according to formula II:

$$-((CH_2)_n-X)_m-(CH_2)_n- \quad [II]$$

wherein m is 0-5,
wherein each n is independently selected from 2-6, and
wherein each X is independently selected from O or S.

19. The polythioether polymer according to claim 13 which is a thiol-terminated polymer.

20. A polythioether polymer comprising divalent groups in the polymer backbone according to formula XXI:

$$-S-R^{21}-S-CH(CH_3)-CH_2-S- \quad [XXI]$$

wherein $R^{21}$ is selected from divalent groups comprising 2-12 carbon atoms, 0-5 ether oxygen atoms and 0-5 thioether sulfur atoms, which may be straight, branched or cyclic.

21. The polythioether polymer according to claim 20 comprising divalent groups in the polymer backbone according to formula XXIII:

$$-S-R^{21}-S-CH(CH_3)-CH_2-S-R^{23}-S- \quad [XXIII]$$

wherein $R^{23}$ is the same group as $R^{21}$.

22. A sealant comprising:
a) the polythioether polymer according to claim 1; and
b) a curing agent.

23. The sealant according to claim 22 wherein the curing agent comprises a polyepoxide.

24. A material obtained by curing a sealant according to claim 22.

* * * * *